United States Patent [19]

Harman

[11] Patent Number: 4,820,267

[45] Date of Patent: Apr. 11, 1989

[54] CARTRIDGE INJECTOR FOR PELLET MEDICAMENTS

[75] Inventor: Sherman M. Harman, Ellicott City, Md.

[73] Assignee: Endocon, Inc., Boston, Mass.

[21] Appl. No.: 703,108

[22] Filed: Feb. 19, 1985

[51] Int. Cl.$^4$ .............................................. A61M 5/18
[52] U.S. Cl. .................................................... 604/60
[58] Field of Search ...................... 604/62, 60, 57–59, 604/61, 63, 64

[56] References Cited

U.S. PATENT DOCUMENTS

| | | | |
|---|---|---|---|
| 939,693 | 11/1909 | Holtzmann | 604/60 |
| 2,513,014 | 11/1946 | Fields . | |
| 2,761,446 | 3/1955 | Reed . | |
| 2,907,327 | 10/1959 | White | 604/60 |
| 3,921,632 | 11/1975 | Bardani | 604/60 |
| 4,086,914 | 5/1978 | Moore | 604/57 |
| 4,105,030 | 8/1978 | Kercso | 604/61 |
| 4,154,239 | 5/1979 | Turley | 604/62 |
| 4,174,048 | 11/1979 | Volpe, Jr. . | |
| 4,223,674 | 9/1980 | Fluent et al. | 604/61 |
| 4,263,910 | 4/1981 | Pardekooper | 604/60 |
| 4,451,253 | 5/1984 | Harman | 604/60 |

Primary Examiner—Stephen C. Pellegrino
Attorney, Agent, or Firm—Wolf, Greenfield & Sacks

[57] ABSTRACT

An improved device for subcutaneous implantation of single and plural elongated medicament pellets comprising a single dosage where magazine feeding is not applicable because considerations of sterility and cross-contamination require a fresh needle and obturator for each patient. The device includes a cannula supported at a proximal end thereof by a hub which slides within a tubular barrel, the barrel supporting an obturator which selectively penetrates the cannula to maintain an implanted pellet in position as the cannula is withdrawn. For single pellet dosages, the pellet is carried in the fore part of the cannula, while in the case of multiple pellet dosages, the additional pellets, prior to loading, are carried in open-ended cylindrical tubes engageable with a proximal end of the hub whereby the obturator may be employed to transfer the pellet to the cannula from the sleeve which is discarded. Repositioning of the hub within the sleeve is then accomplished without disengagement of the distal end of the cannula from the tissues of the patient and additional implantations may then be performed.

2 Claims, 2 Drawing Sheets

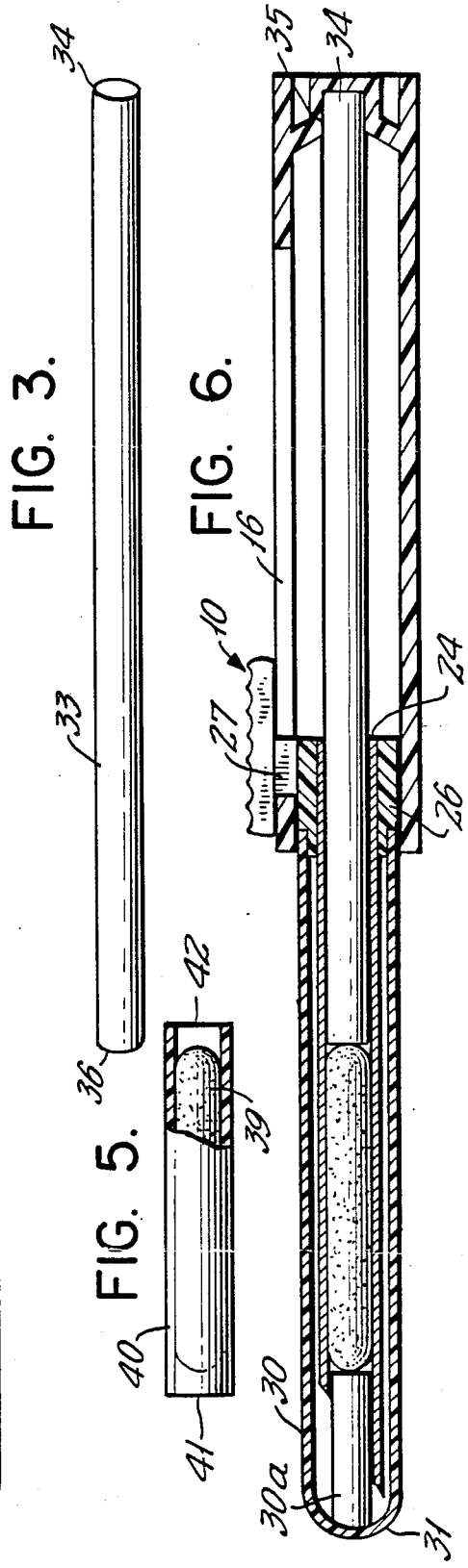

CARTRIDGE INJECTOR FOR PELLET MEDICAMENTS

BACKGROUND OF THE INVENTION

This invention relates generally to the field of devices for the subcutaneous implantation of pellet medicaments of the type described in my prior U.S. Pat. No. 4,451,253 granted Apr. 29, 1984. More particularly, it relates to an improved form thereof particularly suited for the implanting of a plurality of pellets comprising a single dosage into human beings, as contrasted with mechanical type devices used widely in the field of veterinary medicine for administering single dosages serially to plural animals, where problems of sterility are of lesser moment.

One recently developed system of human contraception requires the implantation of a pair of medicament pellets in generally juxtaposed subcutaneous relation. The pellets are of high sectional density, i.e. quite elongated in relation to cross-sectional diameter and may be relatively fragile. For this reason, it is desirable to implant the pellets in a manner in which the implanting needle is withdrawn as the pellet is maintained in position by a relatively non-moving obturator in the manner described in my above-mentioned prior patent. Further, the sterility of both pellets and of the cannula and obturator must be maintained on a continuous basis.

SUMMARY OF THE INVENTION

Briefly stated, the invention contemplates the provision of an improved implanting device of the type described in which the above-mentioned desirata are obtained in which the device may be of disposable single use type thereby eliminating the necessity of sterilization in the field, or in the alternative, where desired, the device may be resterilized between applications and reused. To provide for multiple pellet dosage, the pellets are enclosed and sterilized in open-ended sleeves which are capable of being used as chargers to position additional pellets in the barrel of the device without the necessity of removing the cannula from engagement with the patient. The sleeves allow loading of one or more additional pellets without direct contact between the hand of the operator and the surface of the pellets, thus maintaining the sterility of the pellets.

The device comprises a hub having finger-engaging means whereby it is slidably related to a slotted barrel, one end of which mounts a proximal end of an obturator. The distal end of the obturator penetrates a cannula, the proximal end of which is secured to the hub. Movement of the finger-engaging means relative to the barrel results in the obturator moving through the cannula to maintain an implanted pellet in position as the cannula is withdrawn. The hub is provided with an arcuate recess in a proximal end surface thereof which accommodates an open end of a sleeve carrying a second pellet, so that with the disengagement of the barrel from the hub, the sleeve may be engaged at one end thereof, wherein the distal end of the obturator may be used to move a second pellet into the cannula for subsequent implantation. The barrel is then reengaged with the hub for the implantation of the second pellet after slightly altering the angle of the cannula relative to the site of the implantation. The proximal end of the barrel is of sufficient length that it can accommodate a sleeve engaged in the hub when the hub is fully withdrawn. The sleeve is discarded with the next disengagement of the hub from the barrel.

BRIEF DESCRIPTION OF THE DRAWING

In the drawing to which reference will be made in the specification, similar reference characters have been employed to designate corresponding parts throughout the several views.

FIG. 1 is a view in perspective of a cannula element forming a part of a disclosed embodiment of the invention.

FIG. 2 is a perspective view of a barrel element forming another part of the disclosed embodiment.

FIG. 3 is a perspective view of an obturator member.

FIG. 4 is a perspective view of a cannula cover member.

FIG. 5 is a perspective view of a pellet element and protective sleeve therefor.

FIG. 6 is a longitudinal sectional view of an assembled embodiment in condition for use.

DETAILED DESCRIPTION OF THE DISCLOSED EMBODIMENT

Figure 7:
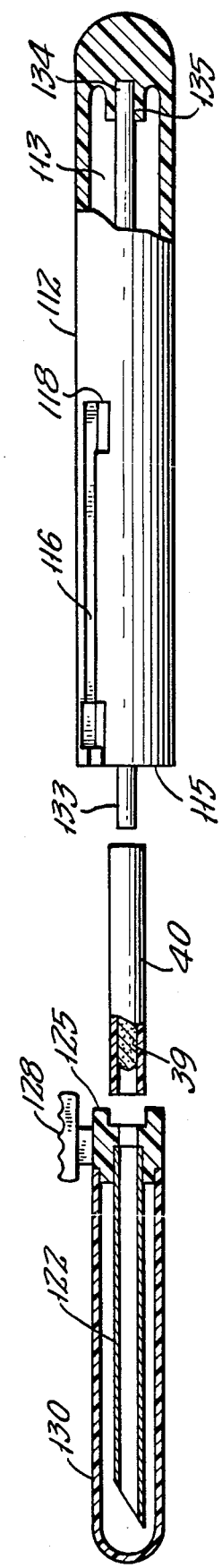
FIG. 7 is an exploded view, partly in section, corresponding to that in FIG. 6, but showing a modified form of the invention.

In accordance with the invention, the device, generally indicated by reference character 10, comprises a barrel element 11 (FIG. 2.) which serves as a manually engageable handle, and may be formed of either metallic or synthetic resinous materials. It is bounded by an outer surface 12, an inner surface 13, a proximal end 14 and a distal end 15. Extending from the distal end 15 is an elongated slot 16 extending between an open end 17 and a closed end 18. The slot includes a distal lock notch and a proximal lock notch, the purpose of which will become more clearly apparent at a later point in this disclosure.

Referring to FIG. 1 in the drawing, a cannula element 21 includes a hollow cannula or needle 22 of inner diameter corresponding to a medicament pellet. It includes a sharpened distal end 23 and a proximal end 24 bonded to a molded hub member 25. The hub member 25 includes a hollow cylindrical body 26 which surrounds the proximal end of the cannula and a laterally extending flange 27 which is conveniently manually engaged by the thumb of the user. A finger-engaging surface 28 thereof may contain suitable grooving for this purpose.

Referring to FIG. 4, although not essential, the cannula element is preferably protected prior to use by a cover member 30, a closed distal end 31 of which may be provided with a peg 30A which enters the distal end of the cannula to maintain a pellet in position during shipping, etc. The open proximal end 32 is preferably frictionally retained upon the hub member 25 until the device is used.

Referring to FIG. 3, a cylindrical obturator 33 is engaged at the proximal end 34 thereof in a retaining well 35 in the barrelelement 11. The distal end 36 is thereby positioned to penetrate the cannula in sliding relation.

Referring to FIG. 5., there is illustrated a medicament pellet element in the form of a cartridge which comprises an elongated medicament pellet 39 and a surrounding polyethylene sleeve 40 having first and second open ends 41 and 42, respectively. Preferably, the sleeve 40 is slightly longer than the pellet 39.

As best seen in FIG. 6., reference character 43 designates a cylindrically-shaped recess in the proximal end 44 of the hub member 25 of diamter corresponding to that of at least one of the open ends 41 and 42.

Where the device is used for implanted multiple elongated pellets as part of a single dosage, the device may be sterilly packed with the first pellet already loaded within the cannula, and the additional required pellets may be packed with surrounding sleeves 40. After removing the cover member 37, the cannula is inserted subcutaneously to a depth sufficient to allow the pellet to be completely implanted (the outer surface of the cannula may be suitably marked for this purpose), following which the flange 27 is moved from the distal lock notch 19 into alignment with the slot 16, and thence to the rear of the proximal lock notch 20. This will result in withdrawal of the cannula while the obturator, entering the cannula maintains the pellet in implanted condition.

While maintaining the distal end of the cannula in engagement with the patient, a reverse motion of the flange permits the barrel element to the disconnected from the hub, and a pellet cartridge element 38 may then be engaged within the recess 43 for reloading. The hub is then reengaged with the barrel element, and after slightly altering the angle of engagement of the cannula with the patient, the implanting action is repeated. The reengagement of the barrel element with the hub will result in engagement by the distal end of the obturator with the free end of the sleeve 40, and the transfer of the pellet 39 to the cannula. Further movement of the hub member 25 within the slot 16 will result in the implantation of the second pellet.

Where the device is used for a single implantation, upon the completion thereof, the hub flange may be engaged with the proximal lock notch to maintain the cannula within the barrel, so that it may be conveniently discarded without danger of injury to personnel.

Turning to the modified form of the invention shown in FIG. 7, parts corresponding to those of the principal form have been designated with a similar reference characters, with the additional prefix "1".

This modification differs from the principal form in the elongation of the barrel 112 and obturator 133 so as to provide additional room for the storing of empty sleeves 40 where the device is used for implanting a plurality of cartridges comprising a pellet and sleeve (FIG. 5). With the additional length, the sleeves 40 may be collapsed and stored in the area indicated by reference character 113, and may be removed, if the device is to be used, by merely disengaging the obturator 133 therefrom.

I wish it to be understood that I do not consider the invention to be limited to the precise details of structure shown and set forth in the proceding specification, for obvious modifications will occur to those skilled in the art to which the invention pertains.

I claim:

1. In a device for subcutaneous implantation of elongated medicament pellets including a cannula, a barrel, open at distal end and closed at a proximal end, surrounding said cannula, and slidably movable relative thereto; and an obturator carried by said barrel at said proximal end, and slidably engaged with said cannula, the improvement comprising: said cannula having a hollow hub surrounding a proximal end thereof, said hub having a laterally extending finger-engaging flange; said barrel element having an elongated axially extending slot having first and second locking notches therein, said flange being slidably disposed within said slot for movement between said notches, whereby said cannula may be selectively immobilized relative to said barrel in first and second positions; said slot in said barrel being open ended to permit disengagement of said cannula from said barrel for the loading of said cannula with a medicament pellet.

2. The improvement in accordance with claim 1, further characterized in said hub having a proximal end surface surrounding a proximal end of said cannula, said surface having engageable means in the form of a circular recess therein; and a pellet element including an elongated pellet and a surrounding tubular sleeve having first and second open ends, at least one of said ends being selectively engageable with said engageable means, engagement serving to align said pellet coaxially with said cannula for transfer thereto.

* * * * *